US006956036B1

(12) United States Patent
May et al.

(10) Patent No.: US 6,956,036 B1
(45) Date of Patent: Oct. 18, 2005

(54) 6-HYDROXY-INDAZOLE DERIVATIVES FOR TREATING GLAUCOMA

(75) Inventors: Jesse A. May, Fort Worth, TX (US); Zixia Feng, Arlington, TX (US); Anura P. Dantanarayana, Fort Worth, TX (US)

(73) Assignee: Alcon, Inc., Hunenberg (CH)

( * ) Notice: Subject to any disclaimer, the term of this patent is extended or adjusted under 35 U.S.C. 154(b) by 0 days.

(21) Appl. No.: 10/221,400

(22) PCT Filed: Nov. 14, 2000

(86) PCT No.: PCT/US00/31247

§ 371 (c)(1),
(2), (4) Date: Mar. 10, 2003

(87) PCT Pub. No.: WO01/70702

PCT Pub. Date: Sep. 27, 2001

Related U.S. Application Data

(60) Provisional application No. 60/190,380, filed on Mar. 17, 2000.

(51) Int. Cl.[7] ................. A61K 31/5375; A61K 31/416; C07D 231/56; C07D 413/04
(52) U.S. Cl. ................. 514/233.8; 514/231.2; 514/406; 544/106; 544/111; 544/140; 544/358; 544/371; 546/184; 546/192; 546/199; 548/356.1; 548/361.1; 548/362.5
(58) Field of Search ................. 548/361.1, 362.5; 514/406, 233.8; 544/140; 546/199

(56) References Cited

U.S. PATENT DOCUMENTS

| | | | |
|---|---|---|---|
| 3,994,890 A * | 11/1976 | Fujimura et al. ........... 544/132 |
| 4,585,869 A * | 4/1986 | Ibuki et al. ................. 546/187 |
| 4,690,931 A | 9/1987 | Wick et al. | |
| 5,151,444 A | 9/1992 | Ueno et al. | |
| 5,296,504 A | 3/1994 | Stjernschantz et al. | |
| 5,352,708 A | 10/1994 | Woodward et al. | |
| 5,422,368 A | 6/1995 | Stjernschantz et al. | |
| 5,494,928 A | 2/1996 | Bös | |
| 5,571,833 A | 11/1996 | Kruse et al. | |
| 5,874,477 A | 2/1999 | McConnell et al. | |
| 5,889,052 A | 3/1999 | Klimko et al. | |
| 5,902,815 A | 5/1999 | Olney et al. | |
| 6,552,062 B1 * | 4/2003 | Adams et al. ............... 514/403 |

FOREIGN PATENT DOCUMENTS

| | | |
|---|---|---|
| EP | 0 985 414 A2 | 3/2000 |
| WO | WO 94/13275 A1 | 6/1994 |
| WO | WO 98/30548 A1 | 7/1998 |
| WO | WO 98/31354 A2 | 7/1998 |
| WO | WO 98/31354 A3 | 7/1998 |
| WO | WO 99/59499 A2 | 11/1999 |
| WO | WO 99/59499 A3 | 11/1999 |
| WO | WO 00/12481 A2 | 3/2000 |
| WO | WO 00/12481 A3 | 3/2000 |
| WO | WO 00/16761 A2 | 3/2000 |
| WO | WO 00/16761 A3 | 3/2000 |
| WO | WO 00/17170 A2 | 3/2000 |
| WO | WO 00/17170 A3 | 3/2000 |
| WO | WO 00/35922 A1 | 6/2000 |

OTHER PUBLICATIONS

Bodar, Nicholas, et al., "Improved Delivery Through Biological Membranes, XVII3. A Site-Specific Chemical Delivery System as a Short-Acting Mydriatic Agent", Pharm. Res., 168-173 (1984).

Bowen et al., "Nonlinear regression using spreadsheets", Trends in Pharmacological Sciences, 16:413-417 (1995).

Florella, et al., "Role of 5-HT2A and 5-HT2C receptors in the stimulus effects of hallucinogenic drugs II: reassessment of LSD false positives", Psychopharmacology, 121:357-363 (1995).

Gever, Gabriel, "Hydrazinoalkanols", J. Amer. Chem. Soc., 76:1283-1285 (1954).

Griffin, B.W., et al., "Pharmacological Characterization of an FP Prostaglandin Receptor on Rat Vascular Smooth Muscle Cells (A7r5) Coupled to Phosphoinositide Turnover and Intracellular Calcium Mobilization", J. Pharmacol. Exp. Ther., 286:411-418 (1998).

Henke, B. R., et al., "Optimization of 3-(1H-Indazol-3-ylmethyl)-1,5-benzodiazepines as Potent, Orally Active CCK-A Agonists", J. Med. Chem., 40:2706-2725 (1997).

Johnson, et al., "Binding To The Serotonin 5-HT2 Receptor By The Enantiomers of 1251-DOI", Neuropharmacology, vol. 26, No. 12, 1803-0806 (1987).

Krapcho, A. P., et al., "Synthesis and Antitumor Evaluation of 2,5-Disubstituted-Indazolo[4,3-gh]isoquinolin-6(2H)-ones (9-Aza-anthrapyrazoles)", J. Med. Chem., 41:5429-5444 (1998).

(Continued)

Primary Examiner—Golam M M Shameem
(74) Attorney, Agent, or Firm—Teresa J. Schultz; Patrick M. Ryan

(57) ABSTRACT

Substituted 1-(α-alkyl-ethylamino)-1H-indazol-6-ols useful for lowering and controlling IOP and treating glaucoma are disclosed

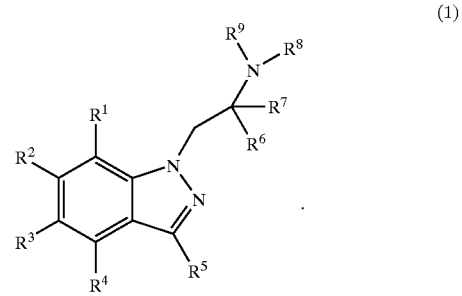

(1)

14 Claims, No Drawings

OTHER PUBLICATIONS

Krapcho, A. P., et al., "Synthesis of Hydroxy-substituted Aza-analogues of Antitumor Anthrapyrazoles", J. Heterocycl. Chem., 35:895-906 (1998).

Sugrue, M.F., "New Approaches to Antiglaucoma Therapy", Journal of Medicinal Chemistry, US, American Chemical Society, Washington, vol. 40, No. 18, pp 2793-2809 (Aug. 29, 1997) [D5].

Wrona, M. Z. and Dryhurst, Glenn, "Further Insights into the Oxidation Chemistry of 5-Hydroxytryptamine", Journal of Pharmaceutical Sciences, 77:911-917 (1988).

Wrona, M. Z. and Dryhurst, G., "Oxidation Chemistry of 5-Hydroxytryptamine. 1, Mechanism and Products Formed at Micromoloar Concentrations" J. Org. Chem, 52:2817-2825 (1987).

\* cited by examiner

6-HYDROXY-INDAZOLE DERIVATIVES FOR TREATING GLAUCOMA

This application claims priority from PCT/US00/31247 filed on Nov. 14, 2000, and U.S. Ser. No. 60/190,380, filed on Mar. 17, 2000.

The present invention is directed to novel substituted 1-(α-alkyl-ethylamino)-1H-indazol-6-ols. These novel compounds are useful for lowering and controlling normal or elevated intraocular pressure (IOP) and treating glaucoma.

BACKGROUND OF THE INVENTION

The disease state referred to as glaucoma is characterized by a permanent loss of visual function due to irreversible damage to the optic nerve. The several morphologically or functionally distinct types of glaucoma are typically characterized by elevated IOP, which is considered to be causally related to the pathological course of the disease. Ocular hypertension is a condition wherein intraocular pressure is elevated but no apparent loss of visual function has occurred; such patients are considered to be a high risk for the eventual development of the visual loss associated with glaucoma. Some patients with glaucomatous field loss have relatively low intraocular pressure. These so called normotension or low tension glaucoma patients can also benefit from agents that lower and control IOP. If glaucoma or ocular hypertension is detected early and treated promptly with medications that effectively reduce elevated intraocular pressure, loss of visual function or its progressive deterioration can generally be ameliorated. Drug therapies that have proven to be effective for the reduction of intraocular pressure include both agents that decrease aqueous humor production and agents that increase the outflow facility. Such therapies are in general administered by one of two possible routes, topically (direct application to the eye) or orally.

There are some individuals who do not respond well when treated with certain existing glaucoma therapies. There is, therefore, a need for other topical therapeutic agents that control IOP.

It has been found that serotonergic compounds which possess agonist activity at 5-$HT_2$ receptors effectively lower and control normal and elevated IOP and are useful for treating glaucoma, see commonly owned co-pending application, PCT/US99/19888. Compounds that act as agonists at 5-$HT_2$ receptors are well known and have shown a variety of utilities, primarily for disorders or conditions associated with the central nervous system (CNS). U.S. Pat. No. 5,494,928 discloses certain 2-(indol-1-yl)-ethylamine derivatives that are 5-$HT_{2C}$ agonists for the treatment of obsessive compulsive disorder and other CNS derived personality disorders. U.S. Pat. No. 5,571,833 discloses tryptamine derivatives that are 5-$HT_2$ agonists for the treatment of portal hypertension and migraine. U.S. Pat. No. 5,874,477 discloses a method for treating malaria using 5-$HT_{2A/2C}$ agonists. U.S. Pat. No. 5,902,815 discloses the use of 5-$HT_{2A}$ agonists to prevent adverse effects of NMDA receptor hypofunction. Published International Patent Application No. WO98/30548 discloses that selected 1-ethylamino-1H-indazoles substituted at ring positions 4-, 5-, 6-, or 7- have selective affinity for the 5-$HT_{2C}$ receptor and thereby have utility in the treatment of central nervous system diseases. International Patent Application Nos. WO00/12481 and WO00/17170 disclose yet other 1-ethylamino-1H-indazoles that have selective affinity for the 5-$HT_{2C}$ receptor and thereby have utility in the treatment of disorders of the central nervous system. Published International Patent Application No. WO98/31354A2 discloses 5-$HT_{2B}$ agonists for the treatment of depression and other CNS conditions. WO00/35922 discloses certain pyrazino[1,2-a]quinoxaline derivatives as 5-$HT_{2C}$ agonists for the treatment of obsessive-compulsive disorder, depression, eating disorders, and other disorders involving the CNS. Agonist response at the 5-$HT_{2A}$ receptor is reported to be the primary activity responsible for hallucinogenic activity, with some lesser involvement of the 5-$HT_{2C}$ receptor possible [Psychopharmacology, Vol. 121:357, 1995].

The present invention is directed to novel substituted 1-(α-alkyl-ethylamino)-1H-indazol-6-ols. It has been determined that these novel compounds have a high affinity for and function as agonists at the serotonergic 5-$HT_2$ receptor, and are useful for lowering and controlling normal or elevated intraocular pressure (IOP) and treating glaucoma. When a phenolic moiety is included in this substitution, e.g. a hydroxyl group at indazole ring position six, such compounds can be particularly sensitive to oxidation reactions well known to occur with phenolic compounds in general, including hydroxytryptamines [*J. Phys. Chem.* 103, 8606 (1999), *Chem. Res. Toxicol.* 11, 639 (1998), *J. Org. Chem.* 52, 2817 (1987), *J. Pharm. Sci.* 77, 911 (1988)], which are of particular relevance to the present application. Protection of such phenyls from oxidation can be accomplished by derivatization of the aryl hydroxyl group to provide a suitable ester, carbamate, or carbonate. Though the ester, carbamate, or carbonate derivatives do not themselves possess a high affinity for the above mentioned receptors, they do have utility in the treatment of glaucoma since suitably protected phenols can be cleaved in vivo either by chemical hydrolysis or through the action of tissue esterases, thereby delivering the desired therapeutic agent, that is, the desired novel 6-hydroxy-indazole compounds of the present invention. The concept of utilizing such derivatized phenolic compounds as chemical delivery agents is well known in the art [*Drugs Pharm. Sci.* 53, 221 (1992), *Pharm. Res.*, 168 (1984)].

SUMMARY OF THE INVENTION

The present invention is directed to new and known derivatives of 1-(ethylamino)-1H-indazole that can be used to lower and control IOP associated with normal-tension glaucoma, ocular hypertension, and glaucoma in warm-blooded animals, including man. The compounds are formulated in pharmaceutical compositions suitable for topical delivery to the eye.

DESCRIPTION OF THE PREFERRED EMBODIMENTS

Compounds that are useful according to the present invention are represented by the following Formula I.

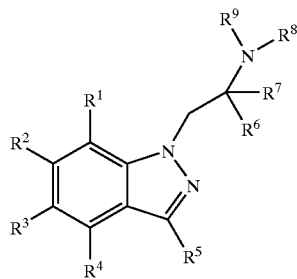

FORMULA I wherein $R^1$ to $R^4$ are independently chosen from hydrogen, halogen, $C_{1-6}$alkyl, trifluoromethyl, O—W, $C_{1-6}$alkylthio, $C_{1-6}$alkylsulfoxyl, $C_{1-6}$alkylsulfonyl, or cyano;

$R^5$ can be hydrogen, $C_{1-6}$alkyl, or $C_{1-4}$alkoxy, halogen, trifluoromethyl, cyano, $NR^{10}R^{11}$;

$R^6$ and $R^7$ are independently chosen from hydrogen, $C_{1-4}$alkyl or $R^6$, $R^7$ and the carbon atom to which they are attached can form a cyclopropyl ring, or furthermore, $R^7$ and $R^8$ together can be $(CH_2)_m$ to form a saturated heterocycle;

$R^8$ and $R^9$ are independently chosen from hydrogen or $C_{1-4}$alkyl;

$R^{10}$ and $R^{11}$ are independently chosen from hydrogen or $C_{1-4}$alkyl, or $R^{10}$, $R^{11}$ and the nitrogen atom to which they are attached can form a saturated heterocyclic ring selected from pyrrolidine, piperidine, piperazine, or morpholine;

$R^1$ to $R^4$ cannot simultaneously be hydrogen;

$R^6$ and $R^7$ cannot both be hydrogen;

W is hydrogen, $C_{1-4}$alkyl, $C(=O)X$, or $P(=O)(OY)(OZ)$;

X is $C_{1-6}$alkyl, $NR^8R^9$, $N(R^8)CH_2(CH_2)_nC(=O)N(R^8)(R^9)$, $OC_{1-6}$alkyl, $C_{1-6}$alkyl (which can be substituted with halogen, hydroxyl, $CO_2C_{1-4}$alkyl, $CON(C_{1-4}$alkyl$)_2$, $C(=NH)NH_2$, $NHC(=NH)NH_2$, $NH_2$), $C_{2-4}$alkenyl (substituted by phenyl, unsubstituted or substituted with one or more of $C_{1-4}$alkyl, $C_{1-4}$alkoxy or halogen);

Y and Z are independently chosen from hydrogen, $C_{1-10}$ alkyl or Y and Z can together form a lower alkyl chain of $(CH_2)_m$;

m is 2–4;

n is 1 or 2;

and pharmaceutically acceptable salts and solvates of the compounds of Formula I.

Compounds that are novel and which are useful according to the present invention can be defined as follows:

wherein $R^1$ to $R^4$ are independently chosen from hydrogen, halogen, $C_{1-6}$alkyl, trifluoromethyl, O—W, $C_{1-6}$alkylthio, $C_{1-6}$alkylsulfoxyl, $C_{1-6}$alkylsulfonyl, or cyano;

$R^5$ can be halogen, trifluoromethyl, cyano, $NR^{10}R^{11}$;

$R^6$ and $R^7$ are independently chosen from hydrogen, $C_{1-4}$alkyl or $R^6$, $R^7$ and the carbon atom to which they are attached can form a cyclopropyl ring, or furthermore, $R^7$ and $R^8$ together can be $(CH_2)_m$ to form a saturated heterocycle;

$R^8$ and $R^9$ are independently chosen from hydrogen or $C_{1-4}$alkyl;

$R^{10}$ and $R^{11}$ are independently chosen from hydrogen or $C_{1-4}$alkyl, or $R^{10}$, $R^{11}$ and the nitrogen atom to which they are attached can form a saturated heterocyclic ring selected from pyrrolidine, piperidine, piperazine, or morpholine;

$R^1$ to $R^4$ cannot simultaneously be hydrogen;

$R^6$ and $R^7$ cannot both be hydrogen;

W is hydrogen, $C_{1-4}$alkyl, $C(=O)X$, or $P(=O)(OY)(OZ)$;

X is $C_{1-6}$alkyl, $NR^8R^9$, $N(R^8)CH_2(CH_2)_nC(=O)N(R^8)(R^9)$, $OC_{1-6}$alkyl, $C_{1-6}$alkyl (which can be substituted with halogen, hydroxyl, $CO_2C_{1-4}$alkyl, $CON(C_{1-4}$alkyl$)_2$, $C(=NH)NH_2$, $NHC(=NH)NH_2$, $NH_2$), $C_{2-4}$alkenyl (substituted by phenyl, unsubstituted or substituted with one or more of $C_{1-4}$alkyl, $C_{1-4}$alkoxy or halogen);

Y and Z are independently chosen from hydrogen, $C_{1-10}$ alkyl or Y and Z can together form a lower alkyl chain of $(CH_2)_m$;

m is 3 or 4;

n is 1 or 2;

and pharmaceutically acceptable salts and solvates of the compounds of Formula I.

Preferred Compounds are:

$R^1$ and $R^2$ are independently chosen from hydrogen, halogen, $C_{1-6}$alkyl, trifluoromethyl, O—W, $C_{1-6}$alkylthio, $C_{1-6}$alkylsulfoxyl, $C_{1-6}$alkylsulfonyl, or cyano;

$R^3$ and $R^4$ are independently chosen from hydrogen, halogen, $C_{1-6}$alkyl, trifluoromethyl, or cyano;

$R^5$ can be hydrogen, $C_{1-4}$alkyl, halogen, trifluoromethyl, or $C_{1-4}$alkoxy;

$R^6$ and $R^7$ are independently chosen from hydrogen or $C_{1-4}$alkyl, or $R^6$, $R^7$ and the carbon atom to which they are attached can form a cyclopropyl ring, or furthermore, $R^7$ and $R^8$ together can be $(CH_2)_m$ to form a saturated heterocycle;

$R^8$ and $R^9$ are independently chosen from hydrogen or $C_{1-4}$alkyl;

$R^1$ to $R^4$ cannot simultaneously be hydrogen;

$R^6$ and $R^7$ cannot both be hydrogen;

W is hydrogen, $C_{1-6}$alkyl, $C(=O)X$, or $P(=O)(OY)(OZ)$, X is $C_{1-6}$alkyl, $NR^8R^9$, $N(R^8)CH_2(CH_2)_nC(=O)NR^8R^9$, $OC_{1-6}$alkyl, $C_{1-6}$alkyl (which can be substituted with halogen, hydroxyl, $CO_2C_{1-4}$alkyl, $CON(C_{1-4}$alkyl$)_2$, $C(=NH)NH_2$, $NHC(=NH)NH_2$, $NH_2$), $C_{2-4}$alkenyl (substituted by phenyl, unsubstituted or substituted with one or more of $C_{1-4}$alkyl, $C_{1-4}$alkoxy or halogen);

Y and Z are independently chosen from hydrogen, $C_{1-10}$alkyl or Y and Z can together form a lower alkyl chain of $(CH_2)_m$;

m is 3;

n is 1 or 2;

The More Preferred Compounds are:

where $R^1$, $R^3$, and $R^4$ are independently chosen from hydrogen, halogen, $C_{1-6}$alkyl, trifluoromethyl, or cyano;

$R^2$ is chosen from O—W;

$R^5$ can be hydrogen, $C_{1-6}$alkyl, halogen, trifluoromethyl, or $C_{1-4}$alkoxy;

$R^6$ is hydrogen and $R^7$ is methyl;

$R^8$ and $R^9$ are independently chosen from hydrogen or $C_{1-4}$alkyl;

W is hydrogen, $C_{1-4}$alkyl, or $C(=O)X$;

X is $C_{1-6}$alkyl, $NR^8R^9$, or $N(R^8)CH_2(CH_2)_nC(=O)N(R^8)(R^9)$;

n is 1 or 2;

The Most Preferred Compounds are:

where $R^1$, $R^3$, and $R^4$ are independently chosen from hydrogen or halogen;

$R^2$ is O—W;

$R^5$ is hydrogen or $C_{1-6}$alkyl;

$R^6$ is hydrogen and $R^7$ is methyl;

$R^8$ and $R^9$ are hydrogen;

W is hydrogen, $C_{1-4}$alkyl;

It is recognized that compounds of Formula I can contain one or more chiral centers. This invention contemplates all enantiomers, diastereomers and, mixtures thereof.

In the above definitions, the total number of carbon atoms in a substituent group is indicated by the $C_{i-j}$ prefix where the numbers i and j define the number of carbon atoms; this definition includes straight chain, branched chain, and cyclic alkyl or (cyclic alkyl)alkyl groups.

It is important to recognize that a substituent may be present either singly or multiply when incorporated into the indicated structural unit. For example, the substituent halogen, which means fluorine, chlorine, bromine, or iodine, would indicate that the unit to which it is attached may be substituted with one or more halogen atoms, which may be the same or different.

Synthesis

The compounds of Formula I can be prepared by processes analogous to those known in the art. The preparation of compounds of Formula I wherein $R^2$ is OH and $R^1$ and $R^3$–$R^5$ are as defined above can be prepared from the appropriate O-protected substituted-indazol-6-ol (1), suitable O-protective groups are e.g. methyl or benzyl, and can be prepared by methods well known in the art and described in Scheme 1 [U.S. Pat. No. 5,494,928 (1997), WO98/30548 (1998)]. Alkylation of indazole 1 with the desired epoxide, e.g. propylene oxide, provides the intermediate alcohol 2. Alternately, it can be advantageous for certain compounds to alkylate 1 using chloroacetone followed by reduction, e.g. with $NaBH_4$, of the intermediate ketone to obtain the intermediate 2.

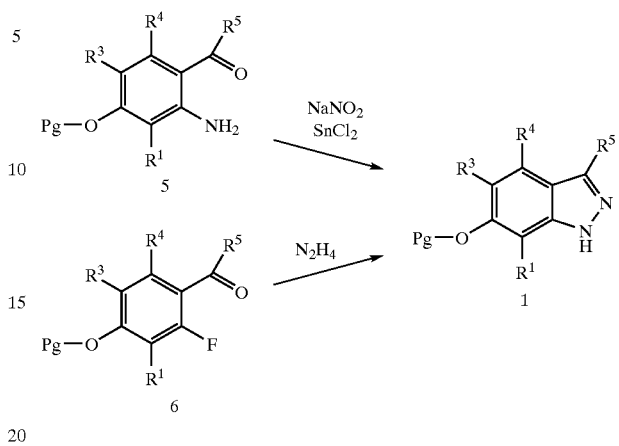

Intermediates 2 of Scheme 1 can also be prepared from the suitably substituted alkoxy-2-fluorophenyl ketones, for example by reaction of 6 with 1-hydrazino-2-propanol [*J.*

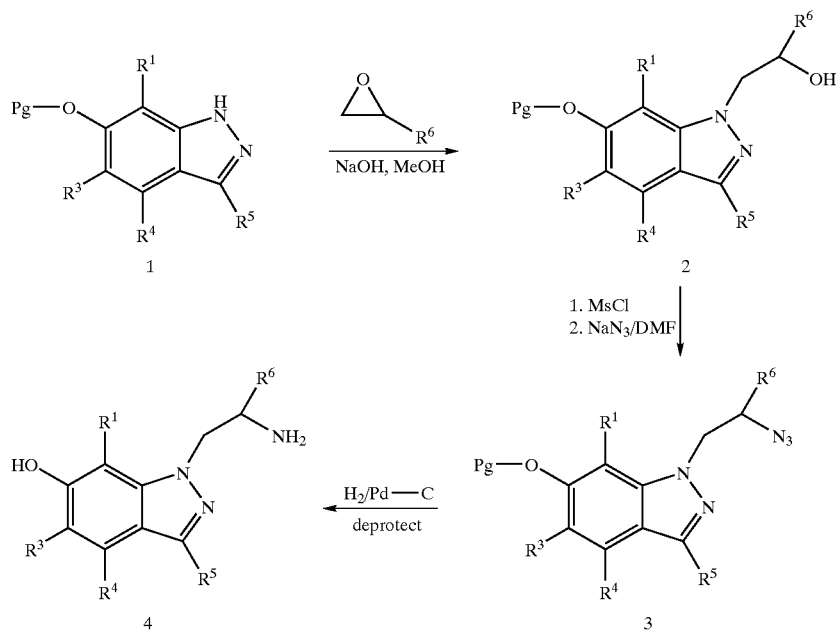

The indazoles 1 can be prepared by conducting suitable functional group transformations on indazoles that are commercially available or that can be prepared according to literature procedures, generally starting from either the desired alkoxy-2-aminophenyl ketone (5), or the suitably substituted alkoxy-2-fluorophenyl ketone (6), depending on availability of suitable precursors (Scheme 2) [*J. Heterocycl. Chem.* 35, 895 (1998); *J. Med. Chem.* 40, 2706 (1997); *Comp. Heterocycl. Chem.* II, Vol. 3, 1 (1996)]. Also, certain indazoles 1 can be prepared from other indazoles 1 by direct substitution or by selective functional group transformations well known to the art.

*Amer. Chem. Soc.* 76, 1283 (1954)] using procedures analogous to those known in the art [*J. Med. Chem.* 41, 5429 (1998)].

The compounds of Formula I wherein $R^2$ is OC(=O)X can be prepared by procedures analogous to those known in the art. For example, when the substituent OC(C=O)X is compatible with the subsequent reaction conditions as described above, such compounds can be prepared as described in Schemes 1 and 2. Alternately, and preferably, compounds of Formula I wherein $R^2$ is OC(=O)X can be prepared by reacting the appropriate indazole 7, or preferably a suitable amino-protected intermediate, e.g. 8 (Scheme 3) with the desired activated acid derivative, such as an acid halide or active ester, or the like, to provide, for example, the esters 9. Removal of the N-protective group from the intermediate 9 provides the desired compounds 10 of Formula I.

philic base prepared from the combination of, for example, carbopol-974, or the like, according to the published formulations for analogous ophthalmic preparations; preservatives and tonicity agents can be incorporated.

SCHEME 3

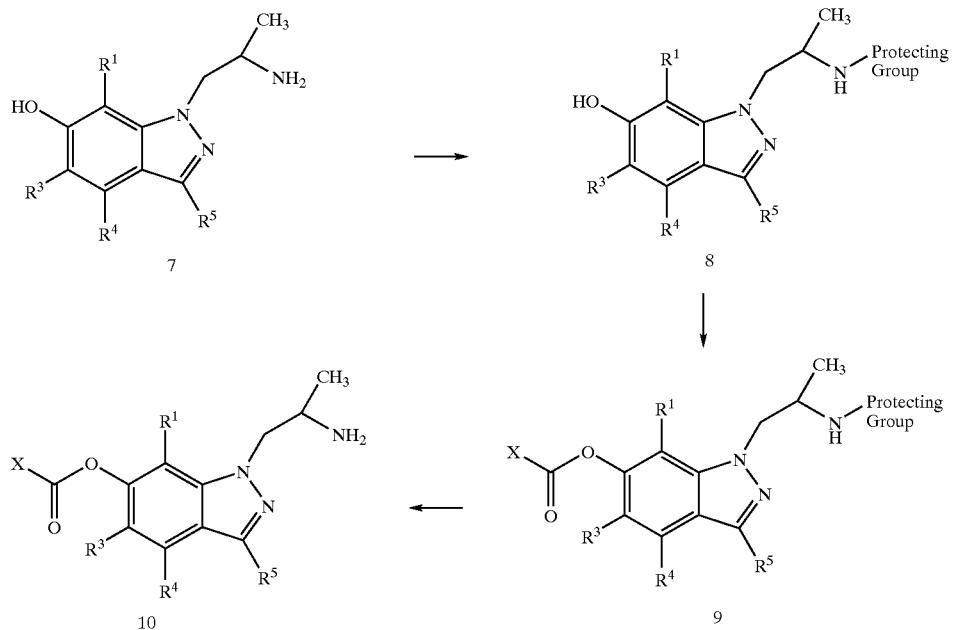

The indazole derivatives of interest for use as starting materials for the preparation of compounds 10 can be prepared by methods described above and in Scheme 1.

The compounds of this invention, Formula I, can be incorporated into various types of ophthalmic formulations for delivery to the eye (e.g., topically, intracamerally, or via an implant). The compounds are preferably incorporated into topical ophthalmic formulations for delivery to the eye. The compounds may be combined with ophthalmologically acceptable preservatives, surfactants, viscosity enhancers, penetration enhancers, buffers, sodium chloride, and water to form an aqueous, sterile ophthalmic suspension or solution. Ophthalmic solution formulations may be prepared by dissolving a compound in a physiologically acceptable isotonic aqueous buffer. Further, the ophthalmic solution may include an ophthalmologically acceptable surfactant to assist in dissolving the compound. Furthermore, the ophthalmic solution may contain an agent to increase viscosity, such as, hydroxymethylcellulose, hydroxyethylcellulose, hydroxypropylmethylcellulose, methylcellulose, polyvinylpyrrolidone, or the like, to improve the retention of the formulation in the conjunctival sac. Gelling agents can also be used, including, but not limited to, gellan and xanthan gum. In order to prepare sterile ophthalmic ointment formulations, the active ingredient is combined with a preservative in an appropriate vehicle, such as, mineral oil, liquid lanolin, or white petrolatum. Sterile ophthalmic gel formulations may be prepared by suspending the active ingredient in a hydro- The compounds are preferably formulated as topical ophthalmic suspensions or solutions, with a pH of about 5 to 8. The compounds will normally be contained in these formulations in an amount 0.01% to 5% by weight, but preferably in an amount of 0.25% to 2% by weight. Thus, for topical presentation 1 to 2 drops of these formulations would be delivered to the surface of the eye 1 to 4 times per day according to the discretion of a skilled clinician.

The compounds can also be used in combination with other agents for treating glaucoma, such as, but not limited to, β-blockers (e.g., timolol, betaxolol, levobetaxolol, carteolol, levobunolol, propranolol), carbonic anhydrase inhibitors (e.g., brinzolamide and dorzolamide), $\alpha_1$ antagonists (e.g. nipradolol), $\alpha_2$ agonists (e.g., iopidine and brimonidine), miotics (e.g., pilocarpine and epinephrine), prostaglandin analogs (e.g., latanoprost, travaprost, unoprostone, and compounds set forth in U.S. Pat. Nos. 5,889,052; 5,296,504; 5,422,368; and 5,151,444, "hypotensive lipids" (e.g., lumigan and compounds set forth in U.S. Pat. No. 5,352,708), and neuroprotectants (e.g., compounds from U.S. Pat. No. 4,690,931, particularly eliprodil and R-eliprodil, as set forth in a pending application U.S. Ser. No. 06/203,350, and appropriate compounds from WO94/13275, including memantine.

The following examples are given to illustrate the preparation of compounds that are the subject of this invention but should not be construed as implying any limitations to the claims. The preferred compounds of Formula I are described in Examples 2, 5 and 7. The most preferred is the compound of Example 2. The proton magnetic resonance spectrum of each compound of the Examples was consistent with the assigned structure.

Method 1

5-HT$_2$ Receptor Binding Assay

In order to determine the relative affinities of serotonergic compounds at the 5-HT$_2$ receptors, their ability to compete for the binding of the agonist radioligand [$^{125}$I]DOI to brain 5-HT$_2$ receptors is determined as described below with minor modification of the literature procedure [Neuropharmacology, 26, 1803 (1987)]. Aliquots of post mortem rat or human cerebral cortex homogenates (400 µl) dispersed in 50 mM TrisHCl buffer (pH 7.4) are incubated with [$^{125}$I]DOI (80 pM final) in the absence or presence of methiothepin (10 µM final) to define total and non-specific binding, respectively, in a total volume of 0.5 ml. The assay mixture is incubated for 1 hour at 23° C. in polypropylene tubes and the assays terminated by rapid vacuum filtration over Whatman GF/B glass fiber filters previously soaked in 0.3% polyethyleneimine using ice-cold buffer. Test compounds (at different concentrations) are substituted for methiothepin. Filter-bound radioactivity is determined by scintillation spectrometry on a beta counter. The data are analyzed using a non-linear, iterative curve-fitting computer program [Trends Pharmacol. Sci., 16, 413 (1995)] to determine the compound affinity parameter. The concentration of the compound needed to inhibit the [$^{125}$I]DOI binding by 50% of the maximum is termed the IC$_{50}$ value. A compound is considered to possess high affinity for the 5-HT$_2$ receptor if the IC$_{50}$ value is less than 50 nM.

Method 2

5-HT$_2$ Functional Assay: Phosphoinositide (PI) Turnover Assay

The relative agonist activity of serotonergic compounds at the 5-HT$_2$ receptor can be determined in vitro using the ability of the compounds to stimulate the production of [$^3$H]inositol phosphates in [$^3$H]myo-inositol-labeled A7r5 rat vascular smooth muscle cells by their ability to activate the enzyme phospholipase C. These cells are grown in culture plates, maintained in a humidified atmosphere of 5% CO$_2$ and 95% air and fed semi-weekly with Dulbecco's modified Eagle medium (DMEM) containing 4.5 g/l glucose and supplemented with 2 mM glutamine, 10 µg/ml gentamicin, and 10% fetal bovine serum. For the purpose of conducting the phosphoinositide (PI) turnover experiments, the A7r5 cells are cultured in 24-well plates as previously [J. Pharmacol. Expt. Ther., 286, 411 (1998)]. Confluent cells are exposed for 24–30 hrs to 1.5 µCi [$^3$H]-myo-inositol (18.3 Ci/mmol) in 0.5 ml of serum-free medium. Cells are then rinsed once with DMEM/F-12 containing 10 mM LiCl prior to incubation with the test agent (or solvent as the control) in 1.0 ml of the same medium for 1 hr at 37° C., after which the medium is aspirated and 1 ml of cold 0.1 M formic acid added to stop the reaction. The chromatographic separation of [3H]-inositol phosphates ([$^3$H]-IPs) on an AG-1-X8 column is performed as previously described [J. Pharmacol. Expt. Ther. 286, 411 (1998)] with sequential washes with H$_2$O and 50 mM ammonium formate, followed by elution of the total [$^3$H]-IPs fraction with 1.2 M ammonium formate containing 0.1 M formic acid. The eluate (4 ml) is collected, mixed with 15 ml scintillation fluid, and the total [$^3$H]-IPs determined by scintillation counting on a beta-counter. Concentration-response data are analyzed by the sigmoidal fit function of the Origin Scientific Graphics software (Microcal Software, Northampton, Mass.) to determine agonist potency (EC$_{50}$ value) and efficacy (E$_{max}$). Serotonin (5-HT) is used as a positive control (standard) agonist compound and the efficacy of test compounds is compared to that of 5-HT (set at 100%). The concentration of the compound needed to stimulate the production of [$^3$H]-IPs by 50% of the maximum response is termed the EC$_{50}$ value. Compounds are considered potent agonists if their EC$_{50}$ values in this functional assay are $\leq 1$ µM and are considered full agonists if their efficacy is >80% of that of 5-HT.

The above procedures were used to generate the data shown in Table 1.

TABLE 1

5-HT$_2$ Receptor Binding and Functional Data.

| Compound | IC$_{50}$, nM | EC$_{50}$, nM | Efficacy (E$_{max}$, %) |
|---|---|---|---|
| α-Methylserotonin | 3.5 | 189 | 104 |
| Example 1 | 3.1 | 578 | 71 |
| Example 2 | 3.0 | 483 | 87 |
| Example 4 | — | 243 | 73 |
| Example 5 | 2.0 | 541 | 64 |
| Example 6 | 2.2 | 1050 | 84 |

EXAMPLE 1

2-(6-Methoxy-3-methyl-indazol-1-yl)-1-methylethylamine Fumarate

Step A: 6-Methoxy-3-methyl-1H-indazole

To a solution of 2-fluoro-4-methoxyacetophenone (1.90 g, 11.3 mmol) in ethanol (20 ml) was added hydrazine hydrate (1.4 ml, 45.0 mmol) and heated at reflux temperature for 6 h. This mixture was evaporated to a residue and ethylene glycol (10 ml) was added. The mixture was heated at 150° C. for 18 h, cooled to room temperature, diluted with water (50 ml), and extracted with dichloromethane (3×60 ml). The combined extracts were washed with brine (10 ml), dried (MgSO$_4$) and evaporated to a residue, which was crystallized from ethyl acetate to give a solid (1.1 g, 59%): MS(ES) m/z 163 (M$^+$).

Step B: 1-(6-Methoxy-3-methyl-indazol-1-yl)-propan-2-one

To a solution of the product from Step A (1.1 g, 6.7 mmol) in DMF (10 ml) was added sodium hydride (60% in oil, 0.41 g, 10.2 mmol) at room temperature. After stirring for 30 min, chloroacetone (0.79 ml, 10.2 mmol) was added, and the solution heated at 60° C. for 6 h. The reaction mixture was diluted with a saturated aqueous solution of ammonium chloride (10 ml) and extracted with ethyl acetate (3×65 ml). The combined extracts were washed with brine (10 ml), dried (MgSO$_4$), and evaporated to give a residue which was purified by chromatography (silica, 20% to 30% ethyl acetate in hexane) to give an oil (1.3 g, 88%): MS (ES) m/z 219 (M$^+$).

Step C: 1-(6-Methoxy-3-methyl-indazol-1-yl)-propan-2-ol

Sodium borohydride (0.21 g, 5.5 mmol) was added to a solution of the product from Step B (1.2 g, 5.5 mmol) in MeOH (10 ml) at room temperature. After stirring for 2 h at room temperature the solvent was evaporated and a saturated aqueous solution of ammonium chloride (10 mL) was added to the residue; this mixture was extracted with ethyl acetate (3×50 mL). The combined extracts were washed with brine (10 ml), dried (MgSO$_4$) and evaporated to a residue which was purified by chromatography (silica, 20% to 30% ethyl acetate in hexane) to give an oil (0.68 g, 56%): MS (ES) m/z 221 (M$^+$).

Step D: 1-(2-Azido-propyl)-6-methoxy-3-methyl-1H-indazole

To a solution of the product from Step C (0.66 g, 3.0 mmol) in dichloromethane (10 ml) at 0° C. was added triethylamine (0.55 ml, 3.9 mmol) and methanesulfonyl chloride (0.31 ml, 3.9 mmol). After stirring for 30 min, ether (50 ml) and water (50 ml) were added. The organic layer was separated and the aqueous extracted with ether (2×50 ml). The combined ether extracts were washed with brine (30 ml), dried (MgSO$_4$), and evaporated. The residue was taken up in DMF (6 ml) and sodium azide (0.26 g, 3.9 mmol) added. This mixture was heated at 70° C. for 12 h, poured into water, and extracted with ether (3×50 ml). The combined extracts were washed with brine, dried (MgSO$_4$), and evaporated to a residue, which was purified by chromatography (silica, hexane to 10% ethyl acetate in hexane) to give an oil (0.51 g, 69%): MS (ES) m/z 246 (M$^+$).

Step E: 2-(6-Methoxy-3-methyl-indazol-1-yl)-1-methylethylamine Fumarate

To a solution of the product from Step D (0.50 g, 2.0 mmol) in methanol at room temperature was added palladium-on-carbon (10%, 0.10 g). This suspension was stirred for 18 h under an atmosphere of hydrogen. The reaction mixture was filtered through a filter aid and the filtrate evaporated to a residue (0.43 g, 96%) which was converted to the fumaric acid salt and crystallized from methanol/ether to give a colorless solid (0.27 g): mp 150–152° C.; MS (ES) m/z 191 (M$^+$). Analysis. Calculated for $C_{12}H_{17}N_3O \cdot 1.0$ $C_4H_4O_4 \cdot 1.0$ $CH_3OH$: C, 55.58; H, 6.86; N, 11.44. Found: C, 55.41; H, 6.85; N, 11.37.

EXAMPLE 2

1-(2-Aminopropyl)-3-methyl-1H-indazol-6-ol Fumarate

Step A: 1-(4-Benzyloxy-2-fluoro-phenyl)-ethanone

Potassium carbonate (5.5 g, 40.0 mmol) and benzyl bromide (4.6 ml, 38.9 mmol) were added to a solution of 2-fluoro-4-hydroxyacetophenone (5.0 g, 32.4 mmol) in ethanol (50 ml), and the mixture was heated at reflux temperature for 16 h. The reaction mixture was evaporated to a residue to which 2 N HCl (100 ml) was added. This mixture was extracted with ethyl ether (3×60 ml) and the combined extracts were washed with brine (10 ml), dried (MgSO$_4$), and evaporated to a residue, which was crystallized from ethyl acetate (7.4 g, 93%): MS(ES) m/z 245 (M$^+$).

Step B: 6-Benzyloxy-3-methyl-1H-indazole

A solution of the product from Step A (7.4 g, 30.3 mmol) in ethanol (20 mL) was treated as described for Example 1, Step A to give a colorless solid (6.1 g, 69%): MS(ES) m/z 239 (M$^+$).

Step C: 1-(6-Benzyloxy-3-methyl-indazol-1-yl)-propan-2-one

A solution of the product from Step B (2.3 g, 9.7 mmol) in DMF (10 ml) was treated by the sequence described for Example 1, Step B to give a residue, which was used in the next step without further purification: MS (ES) m/z 295 (M$^+$).

Step D: 1-(6-Benzyloxy-3-methyl-indazol-1-yl)-propan-2-ol

A solution of the product from Step C (3.3 g, 5.5 mmol) in MeOH (10 ml) was treated as described for Example 1, Step C to give an oil (0.30 g, 10%): MS (ES) m/z 297 (M$^+$).

Step E: 1-(2-Azido-propyl)-6-benzyloxy-3-methyl-1H-indazole

A solution of the product from Step D (0.28 g, 0.95 mmol) in dichloromethane (10 ml) was treated by the sequence described for Example 1, Step D to give an oil (0.16 g, 52%): MS (ES) m/z 322 (M$^+$).

Step F: 1-(2-Aminopropyl)-3-methyl-1H-indazol-6-ol Fumarate

A solution of the product from Step E (0.16 g, 0.50 mmol) in methanol was treated as described for Example 1, Step E to give a residue (0.10 g, 97%) which was converted to fumaric acid salt and crystallized from a mixture of methanol and ether to give a colorless solid (0.11 g): mp:166–168° C.; MS(ES) m/z 206 (M$^+$). Analysis. Calculated for $C_{11}H_{15}N_3O \cdot 1.8$ $C_4H_4O_4$: C, 52.78; H, 5.40; N, 10.15. Found: C, 52.45; H, 5.53; N, 10.29.

EXAMPLE 3

2,2-Dimethyl-propionic Acid 1-(2-aminopropyl)-1H-indazol-6-yl Ester Fumarate

Step A: 2,2-Dimethyl-propionic acid 1H-indazol-6-yl Ester

To a solution of 1H-indazol-6-ol (0.88 g, 6.6 mmol) in dichloromethane (10 ml) at room temperature was added triethylamine (0.98 ml, 7.0 mmol) and DMAP (0.05 g) followed by trimethylacetyl chloride (0.82 ml, 6.6 mmol). After stirring for 1 h, the mixture was diluted with saturated aqueous solution of ammonium chloride (20 ml) and extracted with ethyl acetate (3×50 ml). The combined extracts were washed with brine (10 ml), dried (MgSO$_4$), and evaporated to a residue which was purified by chromatography (silica, 10% to 20% ethyl acetate in hexane) to give an oil (1.1 g, 76%): $^1$H NMR (CDCl$_3$) δ 8.15 (d, J=0.8 Hz, 1H), 8.01 (s, 1H), 7.75 (s, 1H), 7.58 (d, J=8.6 Hz, 1H), 7.01 and 6.96 (dd, J=2.0 and 8.6 Hz, 1H), 1.59 (s, 9H); MS(ES) m/z 219 (M$^+$).

Step B: 2,2-Dimethyl-propionic Acid 1-(2-oxo-propyl)1H-indazol-6-yl Ester

A solution of the product of Step A (1.5 g, 6.9 mmol) in DMF (10 ml) was treated by the procedure described for Example 1, Step B to give an oil (1.3 g, 62%): $^1$H NMR (CDCl$_3$) δ 8.09 (d, J=0.8 Hz, 1H), 7.99 (s, 1H), 7.90 (s, 1H), 7.58 (d, J= 8.6 Hz, 1H), 7.01 and 6.96 (dd, J=2.0 and 8.6 Hz, 1H), 4.64 (s, 2H), 2.15 (s, 3H), 1.56 (s, 3H) 1.27 (s, 6H); MS(ES) m/z 275 (M+).

Step C: 2,2-Dimethyl-propionic Acid 1-(2-hydroxy-propyl)-1H-indazol-6-yl Ester

A solution of the product of Step B (0.91 g, 3.6 mmol) in methanol (10 ml) was treated by the procedure described for Example 1, Step C to give an oil (0.79 g, 86%) that was used in the next reaction with further purification: $^1$H NMR δ (CDCl$_3$) 7.99 (s, 1H), 7.98 (s, 1H), 7.60 (d, J=8.6 Hz, 1H), 7.01 and 6.96 (dd, J=2.0 and 8.6 Hz, 1H,), 4.14–3.89 (m, 3H), 1.56 (s, 3H) 1.32 (s, 9H).

Step D: 2,2-Dimethyl-propionic Acid 1-(2-azido-propyl)-1H-indazol-6-yl Ester

A solution of the product from Step C (1.70 g, 6.2 mmol) in dichloromethane (10 ml) was treated by the procedure described for Example 1, Step D to give an oil (1.30 g, 69%): MS(ES) m/z 274 (M+−28).

Step E: 2,2-Dimethyl-propionic Acid 1-(2-aminopropyl)-1H-indazol-6-yl Ester Fumarate A solution of the Product from Step D (1.25 g, 4.1 mmol) in methanol was treated by the procedure described for Example 1, Step E to give an oil (0.13 g, 88%) which was treated with fumaric acid; the salt which formed was crystallized from a mixture of methanol and ether to give a colorless solid: mp180–182° C.; 1H NMR (DMSO-d$_6$) δ 8.37 (s, 1H), 7.89 (s, 1H), 7.82 (d, J=8.6 Hz, 1H), 7.12 (d, J=8.6 Hz, 1H), 6.45 (s, 2H), 4.18 –4.01 (m, 2H), 3.5 (m, 1H), 1.50 (s, 9H) 1.30 (d, J=6.6 Hz, 3H); MS(ES) m/z 276 (M+). Analysis. Calculated for $C_{15}H_{21}N_3O_2 \cdot 1.2\ C_4H_4O_4$: C, 57.36; H, 6.27; N, 10.13. Found: C, 56.98; H, 6.57; N, 10.22.

EXAMPLE 4

2-(6-Methoxy-indazol-1-yl)-1-methyl-ethylamine

Step A: [2-(6-Hydroxy-indazol-1-yl)-1-methyl-ethyl]-carbamic Acid Benzyl Ester

To a solution of 1-(2-aminopropyl)-indazol-6-ol (0.46 g, 2.4 mmol) in THF (10.0 mL) was added a saturated aqueous solution of sodium bicarbonate (2.0 mL) followed by benzyl chloroformate (0.40 mL) at room temperature. After stirring for 1 h, the solution was diluted with 1 N HCl (10 mL) and ammonium chloride (20 mL) followed by extraction with ethyl acetate (3×50 mL). The combined extracts were washed with brine (10 mL), dried (MgSO$_4$) and evaporated to give a residue which was used in the next step without further purification (0.75 g, 98%); MS (ES) m/z 326 (M+).

Step B: [2-(6-Methoxy-indazol-1-yl)-1-methyl-ethyl]-carbamic Acid Benzyl Ester

To a solution of the product from Step A (0.95 g, 3.19 mmol) in DMF (10 mL) was added cesium carbonate (1.26 g, 3.70 mmol) followed by iodomethane (0.23 mL, 3.70 mmol) at room temperature. After stirring for 3 h, saturated aqueous ammonium chloride (30 mL) was added and the mixture extracted with ethyl acetate (3×65 mL). The combined extracts were washed with brine (10 mL), dried (MgSO$_4$) and evaporated to a residue which was purified by chromatography (silica, 20% ethyl acetate in hexane to 30% ethyl acetate in hexane) to give a syrup (0.63 g, 92%): MS (ES) m/z 340(M+).

Step C: 2-(6-Methoxy-indazol-1-yl)-1-methyl-ethylamine

To a solution of the product from Step B (0.68 g, 2.0 mmol) in methanol was added Pd/C (10%, 0.10 g) under a nitrogen atmosphere at room temperature. The mixture was stirred for 20 h under a hydrogen atmosphere and filtered through a filter aid. The filtrate was evaporated to a residue which was purified by chromatography (silica, 5% methanol in dichloromethane to 10% methanol in dichloromethane) to give a syrup (0.40 g, 97%). Treatment of the syrup with fumaric acid gave a residue that was recrystallized from methanol/ether to provide a colorless solid: mp 151–152° C.; MS (ES) m/z 206 (M+). Analysis. Calculated for $C_{11}H_{15}N_3O \cdot 1.0\ C_4H_4O_4 \cdot 1.0H_2O$: C, 53.09; H, 6.24; N, 12.38. Found: C, 52.88; H, 6.31; N, 12.14.

EXAMPLE 5

2-(3-Chloro-6-methoxy-indazol-1-yl)-1-methyl-ethylamine

Step A: 2-Hydrazino-4-methoxy-benzoic Acid

A suspension of 2-acetylamino-4-methoxy-benzoic acid (15 g, 73.7 mmol) in water (75 mL) was cooled to −5° C. and conc HCl (150 mL) was added followed by cooling to −5°. To this mixture was added a solution of NaNO$_2$ (5.43 g, 77.4 mmol) in water (50 mL) that had been cooled to −5°; this solution was added at such a rate so as to maintain the temperature of the reaction mixture between −5° and 0° C. The reaction mixture was stirred for 10 min and the clear solution was added to a solution of stannous chloride (41.9 g, 221 mmol) in conc HCl (150 mL) that had been cooled to −20° C. This addition was conducted so as to maintain a temperature of −20° to − 10° C. for the reaction mixture, followed by stirring the mixture for 1.5 h at −20° C. The solid that formed was collected by filtration, washed with chilled EtOH, and dried to give an off-white solid (10.8 g): APCl/LCMS m/z 183 (M+H)+.

Step B: 6-Methoxy-1H-indazol-3-ol

A mixture of the product from Step A (10.5 g, 48 mmol), water (250 mL), and conc HCl (2.5 mL) was refluxed for 30 min. The volume of the reaction mixture was reduced by evaporation (ca 100 mL) and the pH adjusted to 7 by the slow addition of a saturated aqueous solution of sodium carbonate at room temperature. The solid that formed upon standing was collected and dried to give a gray solid (6.8 g): APCl/LCMS m/z 165 (M+H)+.

Step C: 3-Chloro-6-methoxy-1H-indazole

To a solution of the product from Step B (1 g, 6.1 mmol) in pyridine (0.5 mL, 6.1 mmol) was added phosphorous oxychloride (0.9 mL, 9.2 mmol) and the mixture heated at 130–140° C. for 5 h. The reaction mixture was cooled to 70° C. and poured onto ice (100 g). After standing for 24 h, the solid was collected and dried to give a cream-colored solid (0.42 g): ES/LCMS m/z 181 (M−H)+.

Step D: [2-(3-Chloro-6-methoxy-indazol-1-yl)-1-methyl-ethyl]-carbamic Acid Benzyl Ester To a solution of the product from Step C (0.18 g, 1 mmol) and (2-bromo-1 methyl-ethyl)-carbamic acid benzyl ester (0.27 g, 1 mmol) in DMF (2 mL) was added potassium carbonate (0.17 g, 1.2 mmol) and the mixture stirred at 75° for 18 h. Ethyl acetate (20 mL) and water (20 mL) were added to the reaction mixture and the aqueous layer was separated and extracted with ethyl acetate (3×20 mL). The combined extracts were washed with brine (30 mL), dried ($MgSO_4$), and evaporated to a residue that was purified by chromatography (silica, hexane to 15% ethyl acetate in hexane) to give a syrup (0.27 g): APCI/LCMS m/z 374 $(M+H)^+$.

Step E: 2-(3-Chloro-6-methoxy-indazol-1-yl)-1-methyl-ethylamine

To a solution of the product from Step D (0.15 g, 0.4 mmol) in 1,2-dichloroethane (4 mL) under nitrogen was added boron tribromide-dimethylsulfide complex (2.4 mmol, 2.4 mL of a 1 N solution in 1,2-dichloroethane) and the mixture was heated at 84° C. for 3 h. After cooling, saturated aqueous sodium bicarbonate (5 mL) was added and the mixture was extracted with chloroform (3×10 mL). The combined extracts were washed with brine (10 mL), dried ($MgSO_4$), and purified by chromatography (C-18 RP-HPLC, 5% acetonitrile/water to 70% acetonitrile/water containing 0.1% trifluoroacetic acid) to give a residue (0.03 g) that was converted to the dihydrochloride salt: ESI/LCMS m/z 240 $(M+H)^+$.

EXAMPLE 6

1-(2-Aminopropyl)-3-chloro-1H-indazol-6-ol

A solution of the product from Example 5, Step D (0.1 g, 0.27 mmol) was treated as described in Step E of Example 5 but the reaction mixture was heated for 8 h to give a syrup (0.015 g), which was converted to the dihydrochloride salt: ESI/LCMS m/z 226 $(M+H)^+$.

| Ingredients | Amount (wt %) |
|---|---|
| 1-(2-Aminopropyl)-3-methyl-1H-indazol-6-ol fumarate | 0.01–2% |
| Hydroxypropyl methylcellulose | 0.5% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.4 |
| Purified water | q.s. to 100% |

| Ingredients | Amount (wt %) |
|---|---|
| 1-(2-Aminopropyl)-3-methyl-1H-indazol-6-ol fumarate | 0.01–2% |
| Methyl cellulose | 4.0% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.4 |
| Purified water | q.s. to 100% |

| Ingredients | Amount (wt %) |
|---|---|
| 1-(2-Aminopropyl)-3-methyl-1H-indazol-6-ol fumarate | 0.01–2% |
| Guar gum | 0.4–6.0% |
| Dibasic sodium phosphate (anhydrous) | 0.2%– |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH |
| Purified water | q.s. to 100% |

| Ingredients | Amount (wt %) |
|---|---|
| 1-(2-Aminopropyl)-3-methyl-1H-indazol-6-ol fumarate | 0.01–2% |
| White petrolatum and mineral oil and lanolin | Ointment consistency |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH |

What is claimed is:

1. A compound of the formula:

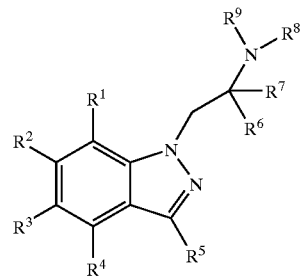

wherein $R^1$ to $R^4$ are independently chosen from hydrogen, halogen, $C_{1-6}$ alkyl, trifluoromethyl, O—W, $C_{1-6}$ alkylthio, $C_{1-6}$ alkylsulfoxyl, $C_{1-6}$ alkylsulfonyl, or cyano;

$R^5$ is halogen, trifluoromethyl, cyano, or $NR^{10}R^{11}$;

$R^6$ and $R^7$ are independently chosen from hydrogen, $C_{1-4}$ alkyl or $R^6$, $R^7$ and the carbon atom to which they are attached form a cyclopropyl ring, or furthermore, $R^7$ and $R^8$ together are $(CH_2)_m$ to form a saturated heterocycle;

$R^8$ and $R^9$ are independently chosen from hydrogen or $C_{1-4}$ alkyl;

$R^{10}$ and $R^{11}$ are independently chosen from hydrogen or $C_{1-4}$ alkyl, or $R^{10}$, $R^{11}$ and the nitrogen atom to which they are attached form a saturated heterocyclic ring selected from pyrrolidine, piperidine, piperazine, or morpholine;

$R^1$ to $R^4$ are not simultaneously hydrogen;

$R^6$ and $R^7$ are not both hydrogen;

W is hydrogen, $C_{1-4}$ alkyl, C(=O)X, or P(=O)(OY)(OZ);

X is $C_{1-6}$alkyl, $NR^8R^9$, $N(R^8)CH_2(CH_2)_nC(=O)N(R^8)(R^9)$, $OC_{1-6}$ alkyl, $C_{1-6}$alkyl, $C_{2-4}$ alkenyl, wherein said $C_{1-6}$ alkyl is optionally substituted with halogen, hydroxyl, $CO_2C_{1-4}$ alkyl, $CON(C_{1-4}$ alkyl$)_2$, C(=NH)NH$_2$, NHC(=NH)NH$_2$, or NH$_2$, and wherein said $C_{2-4}$ alkenyl is optionally substituted by phenyl, unsubstituted or substituted with one or more of $C_{1-4}$ alkyl, $C_{1-4}$ alkoxy or halogen;

Y and Z are independently chosen from hydrogen, $C_{1-10}$ alkyl or Y and Z together form a lower alkyl chain of $(CH_2)_m$;

m is 3 or 4;

n is 1 or 2;

and pharmaceutically acceptable salts and solvates of the compound.

2. The compound of claim 1 wherein:

$R^1$ and $R^2$ are independently chosen from hydrogen, halogen, $C_{1-6}$ alkyl, trifluoromethyl, O—W, $C_{1-6}$ alkylthio, $C_{1-6}$ alkylsulfoxyl, $C_{1-6}$ alkylsulfonyl, or cyano;

$R^3$ and $R^4$ are independently chosen from hydrogen, halogen, $C_{1-6}$ alkyl, trifluoromethyl, or cyano;

$R^5$ is halogen or trifluoromethyl;

$R^6$ and $R^7$ are independently chosen from hydrogen or $C_{1-4}$ alkyl, or $R^6$, $R^7$ and the carbon atom to which they are attached form a cyclopropyl ring, or furthermore, $R^7$ and $R^8$ together are $(CH_2)_m$ to form a saturated heterocycle;

$R^8$ and $R^9$ are independently chosen from hydrogen or $C_{1-4}$ alkyl;

$R^1$ to $R^4$ are not simultaneously hydrogen;

$R^6$ and $R^7$ are not both hydrogen;

W is hydrogen, $C_{1-6}$ alkyl, C(=O)X, or P(=O)(OY)(OZ), X is $C_{1-6}$ alkyl, $NR^8R^9$, $N(R^8)CH_2(CH_2)_nC(=O)NR^8R^9$, $OC_{1-6}$ alkyl, $C_{1-6}$ alkyl, $C_{2-4}$ alkenyl, wherein said $C_{1-6}$ alkyl is optionally substituted with halogen, hydroxyl, $CO_2C_{1-4}$ alkyl, $CON(C_{1-4}$ alkyl$)_2$, C(=NH)NH$_2$, NHC(=NH)NH$_2$, or NH$_2$, and wherein said $C_{2-4}$ alkenyl is optionally substituted by phenyl, unsubstituted or substituted with one or more of $C_{1-4}$ alkyl, $C_{1-4}$ alkoxy or halogen;

Y and Z are independently chosen from hydrogen, $C_{1-10}$ alkyl or Y and Z together form a lower alkyl chain of $(CH_2)_m$;

m is 3;

n is 1 or 2.

3. The compound of claim 1 wherein:

$R^1$, $R^3$, and $R^4$ are independently chosen from hydrogen, halogen, $C_{1-6}$ alkyl, trifluoromethyl, or cyano;

$R^2$ is chosen from O—W;

$R^5$ is halogen or trifluoromethyl;

$R^6$ is hydrogen and $R^7$ is methyl;

$R^8$ and $R^9$ are independently chosen from hydrogen or $C_{1-4}$ alkyl;

W is hydrogen, $C_{1-4}$alkyl, or C(=O)X;

X is $C_{1-6}$ alkyl, $NR^8R^9$, or $N(R^8)CH_2(CH_2)_nC(=O)N(R^8)(R^9)$;

n is 1 or 2.

4. The compound of claim 1 wherein:

$R^1$, $R^3$, and $R^4$ are independently chosen from hydrogen or halogen;

$R^2$ is O—W;

$R^5$ is halogen or trifluoromethyl;

$R^6$ is hydrogen and $R^7$ is methyl;

$R^8$ and $R^9$ are hydrogen;

W is hydrogen, $C_{1-4}$ alkyl.

5. The compound of claim 1, wherein said compound is:
1-(2-aminopropyl)-3-chloro-1H-indazol-6-ol fumarate or
2-(3-chloro-6-methoxy-indazol-1-yl)-1-methyl-ethylamine.

6. A topical ophthalmic composition for lowering and controlling normal or elevated intraocular pressure and treating glaucoma, comprising a pharmaceutically effective amount of a compound of claim 1, 2, 3, 4, or 5 and a pharmaceutically acceptable carrier or diluent.

7. Composition according to claim 6 containing additionally one or more other agents for treating glaucoma.

8. Composition according to claim 7 in which the other agent is selected from the group consisting of β-blockers, carbonic anhydrase inhibitors, α$_1$ antagonists, α$_2$ agonists, miotics, prostaglandin analogs, hypotensive lipids, and neuroprotectants.

9. Composition according to claim 7 in which the other agent is one or more of the following: timolol, betaxolol, levobetaxolol, carteolol, levobunolol, propranolol, brinzolamide, dorzolamide, nipradolol, iopidine, brimonidine, pilocarpine, epinephrine, latanoprost, travaprost, unoprostone, lumigan, eliprodil and R-eliprodil.

10. A method of controlling normal or elevated intraocular pressure or treating glaucoma, comprising administering a pharmaceutically effective amount of a compound of claim 1, 2, 3, 4, or 5.

11. A method of controlling normal or elevated intraocular pressure or treating glaucoma comprising administering a pharmaceutically effective amount of a compound of the formula:

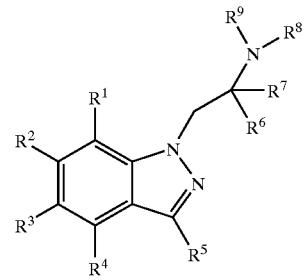

wherein $R^1$ to $R^4$ are independently chosen from hydrogen, halogen, $C_{1-6}$ alkyl, trifluoromethyl, O—W, $C_{1-6}$ alkylthio, $C_{1-6}$ alkylsulfoxyl, $C_{1-6}$ alkylsulfonyl, or cyano;

$R^5$ is hydrogen, $C_{1-6}$ alkyl, $C_{1-6}$ alkoxy, halogen trifluoromethyl, cyano, or $NR^{10}R^{11}$;

$R^6$ and $R^7$ are independently chosen from hydrogen, $C_{1-4}$ alkyl or $R^6$, $R^7$ and the carbon atom to which they are attached form a cyclopropyl ring, or furthermore, $R^7$ and $R^8$ together are $(CH_2)_m$ to form a saturated heterocycle;

$R^8$ and $R^9$ are independently chosen from hydrogen or $C_{1-4}$ alkyl;

$R^{10}$ and $R^{11}$ are independently chosen from hydrogen or $C_{1-4}$ alkyl, or $R^{10}$, $R^{11}$ and the nitrogen atom to which they are attached form a saturated heterocyclic ring selected from pyrrolidine, piperidine, piperazine, or morpholine;

$R^1$ to $R^4$ are not simultaneously hydrogen;

$R^6$ and $R^7$ are not both hydrogen;

W is hydrogen, $C_{1-4}$ alkyl, C(=O)X, or P(=O)(OY)(OZ);

X is $C_{1-6}$ alkyl, $NR^8R^9$, $N(R^8)CH_2(CH_2)_nC(=O)N(R^8)(R^9)$, $OC_{1-6}$ alkyl, $C_{1-6}$ alkyl, $C_{2-4}$ alkenyl, wherein said $C_{1-6}$ alkyl is optionally substituted with halogen, hydroxyl, $CO_2C_{1-4}$ alkyl, $CON(C_{1-4}$ alkyl$)_2$, C(=NH)$NH_2$, NHC(=NH)$NH_2$, or $NH_2$, $C_{2-4}$ alkenyl and wherein said $C_{2-4}$ alkenyl is optionally substituted by phenyl, unsubstituted or substituted with one or more of $C_{1-4}$ alkyl, $C_{1-4}$ alkoxy or halogen;

Y and Z are independently chosen from hydrogen, $C_{1-10}$ alkyl or Y and Z together form a lower alkyl chain of $(CH_2)_m$;

m is 2–4;

n is 1 or 2;

and pharmaceutically acceptable salts and solvates of the compounds.

12. The method of claim 10 or 11, wherein said compound is administered in combination with one or more other agents for treating glaucoma.

13. The method of claim 12 in which the other agent is selected from the group consisting of β-blockers, carbonic anhydrase inhibitors, $\alpha_1$ antagonists, $\alpha_2$ agonists, miotics, prostaglandin analogs, hypotensive lipids, and neuroprotectants.

14. The method of claim 12 in which the other agent is one or more of the following: timolol, betaxolol, levobetaxolol, carteolol, levobunolol, propranolol, brinzolamide, dorzolamide, nipradolol, iopidine, brimonidine, pilocarpine, epinephrine, latanoprost, travoprost, unoprostone, lumigan, eliprodil or R-eliprodil.

* * * * *